United States Patent [19]
Brown et al.

[11] Patent Number: 5,746,214
[45] Date of Patent: May 5, 1998

[54] INVESTIGATION OF A BODY

[75] Inventors: Brian Hilton Brown; David Charles Barber, both of Sheffield, England

[73] Assignee: British Technology Group Limited, London, England

[21] Appl. No.: 416,717

[22] PCT Filed: Oct. 28, 1993

[86] PCT No.: PCT/GB93/02223

§ 371 Date: May 30, 1995

§ 102(e) Date: May 30, 1995

[87] PCT Pub. No.: WO94/09699

PCT Pub. Date: May 11, 1994

[30] Foreign Application Priority Data

Oct. 30, 1992 [GB] United Kingdom .................... 9222888

[51] Int. Cl.$^6$ ........................................ A61B 5/02
[52] U.S. Cl. ........................................ 128/693
[58] Field of Search ................... 128/693, 723, 128/734, 898, 897

[56] References Cited

U.S. PATENT DOCUMENTS

| | | | |
|---|---|---|---|
| 3,253,588 | 5/1966 | Vuilleumier et al. | |
| 4,793,362 | 12/1988 | Tedner | 128/734 |
| 5,063,937 | 11/1991 | Ezenwa et al. | 128/734 X |
| 5,282,840 | 2/1994 | Hudrlik | 128/734 |
| 5,449,000 | 9/1995 | Libke et al. | 128/734 |
| 5,526,808 | 6/1996 | Kaminsky | 128/693 X |

FOREIGN PATENT DOCUMENTS 2160323 12/1985 United Kingdom .
9119454 12/1991 WIPO .

OTHER PUBLICATIONS

Kanai et al., "Electrical measurement of fluid distribution in legs and arms", Medical Process through Technology, 12:159–170 (1987).

Poc. 11th Ann. Conf. of the IEEE Eing. In Med. and Biol. Society. vol. 11, 12 Nov. 1989, Seattle, WA (US) pp. 476–477, H.Griffiths et al. "Dual–Frequency Eit in vitro and in Vivo".

Proc. Ninth Ann.Conf. of the IEEE Eng. In Med. and Biol Soc., vol. 9, 16 Nov. 1987, Boston, MA (US) pp. 1416–1417 Zhili Huang et al. Bioimpedance Measurement: Theory, Experiment and Application.

Clinical Physics and Physiological Measurement, Supplement A, vol. 13, 1992, pp. 67–72, P.M.Record et al "Multifrequency Electrical Impedance tomography" cited in the Appln., Abstract and Section 6. Demonstration.

IEEE Eng. In Medicine and Biology, vol. 8, No. 1, Mar. 1989, New York (US) pp. 11–15, XP2285 L.E. Baker, "Principles of Impedance Technique" Sections Reactive Component in bioimpedance and Impedance Imaging.

*Primary Examiner*—Jennifer Bahr
*Assistant Examiner*—Samuel Gilbert
*Attorney, Agent, or Firm*—Cushman, Darby & Cushman IP Group of Pillsbury, Madison & Sutro LLP

[57] ABSTRACT

A method of investigation of a body including applying interrogatory electrical signals at different frequencies to the body. First signals are obtained representing first electrical impedance measurements at the different frequencies. Second signals are obtained representing subsequent second electrical impedance measurements at the different frequencies after a change in the internal state of the body. Characteristics of part of the body are selectively determined in response to the first and second signals at the different frequencies. The invention has application in electrical impedance tomography techniques where the different frequency behavior of different parts of the body associated with temporal changes can be used to improve organ resolution and tissue differentiation.

15 Claims, 6 Drawing Sheets

9·6kHz

19·2kHz

38·4kHz

76·8kHz

153·6kHz

307·2kHz

614·4kHz

1228·8kHz

INVESTIGATION OF A BODY

BACKGROUND OF THE INVENTION

Field of the invention

This invention concerns investigation of a body. More specifically it is related to tomography and particularly to electrical impedance tomography or so-called EIT.

DESCRIPTION OF THE RELATED ART

EIT as currently developed (see B. H. Brown and D. C. Barber, Electrical ImpedanceTomography, Clin. Phys. and Physiol Meas. 13, Suppl. A., pp.207, 1992) uses an array of electrodes placed around a body, which is normally that of a human patient, to produce an image of changes in tissue resistivity or impedance. It has been shown that both cardiac and respiratory related changes can be imaged. The respiratory related changes arise mainly from the lungs but the cardiac related changes arise from the heart, the lungs and the major blood vessels. The changes from the heart arise from large changes in blood volume. The changes from the blood vessels are due mainly to changes in cross sectional area, and hence blood volume, as the pulse pressure changes. Changes from the lungs are also associated with blood volume changes as the pressure on systole increases the blood content of the pulmonary tree. EIT images of cardiac and respiratory related changes have been made at a single frequency within the range 20–50 kHz. International application WO91/19454 describes a real-time EIT system applicable to the investigation of dynamic systems, such as the observation of blood flow in the human body during the cardiac cycle.

Several EIT research groups are now considering making images from measurements made over a range of frequencies, with a view to reducing the effects of body geometry on the images and also in the hope that tissue can be characterized in terms of how its impedance changes with frequency. Such work is described in, among other papers, P. M. Record, R. Gadd and F. Vinther, Multi-frequency EIT, Clin. Phys. and Physiol. Meas. 13, Suppl. A, pp.67–72 (1992). H. Griffiths and Z. Zhang, Dual-Frequency Electrical Impedance Tomography in Vitro and in Vivo, Proc. 11th Ann. Conf. of the IEEE Eng. in Med. and Biol. Society, Vol. 11, 12 November 1989, pp. 476–477, similarly describes imaging using dual-frequency EIT.

SUMMARY OF THE INVENTION

The present invention derives from investigations of electrical impedance measurements made on the human trunk over a wide frequency range which have led to results of an unexpected nature. This work was directed towards the study of changes of impedance occurring over a change in the internal state of a body measured at different electrical signal frequencies.

According to the invention there is provided a method of investigation of a body comprising:
- applying interrogatory electrical signals at different frequencies to the body;
- obtaining first signals representing first electrical impedance measurements at the different frequencies;
- obtaining second signals representing subsequent second electrical impedance measurements at the different frequencies after a change in the internal state of the body; and
- selectively determining characteristics of part of said body in response to the first and second signals at the different frequencies.

The work referred to above and described in greater detail below has led to the surprising finding, hitherto not appreciated, that there can be a significant difference in the way in which impedance changes in a dynamic system vary with frequency, depending on which part of the system the impedance or impedance change is associated with.

More specifically, in the case of in vivo investigations of the human or animal body and considering impedances in the trunk of the body, as the frequency increases, the impedance change associated with the cardiac cycle falls considerably more rapidly than that associated with the respiratory cycle. This phenomenon has not anticipated by any studies hitherto made. The temporal change in impedance associated with different dynamic features of the body is found to be a function of frequency, the function depending on which dynamic feature the impedance change is associated with.

In most cases, the change in an internal state of the body is a change in the geometry of at least a part of the body. For example, in the human body, such changes may be changes in the cross sectional area of blood vessels due to a pulsatile blood flow. Alternatively, such changes may be changes in the air volume, and hence, the size of the lungs, or changes in blood volume in the heart. Non medical or veterinary applications of the invention are also envisioned.

Preferably the electrical impedance measurements are made at selected different points in a cyclic change in the internal state of the body. Preferably, these points are selected to correspond substantially to the peak and trough of the cyclic fluctuation in impedance associated with the cyclic change.

In the case of the human body, the respective signals can be obtained by taking measurements in synchronization with a cyclic variation in the state of a particular body part. For example, cardiosynchronous signals can be related to the heart, the measurements being synchronized with a point in the subject's ECG wave, while measurements synchronized with a subject's inspiration and expiration can be related to the lungs.

Preferably, the signal representations obtained represent only the real part of the impedance measurements. In many cases, it is thought that the capacitive components of impedance measurements can be prone to errors and are therefore unreliable.

In a developed form of the invention, the method involves generating a tomographic image of the body part using signals representing the characteristics of the body part.

The observed phenomenon can, for example, be used in generating tomographic images of a cross section of a human body. By taking advantage of the different frequency behavior of organs associated with temporal changes, organ resolution and tissue differentiation can be improved.

The electrical signals are suitably in the kHz frequency range with there preferably being at least one order of numerical difference between the lowest and highest frequencies. It is considerably easier to work in the kHz range than in the MHz range.

BRIEF DESCRIPTION OF THE DRAWINGS

Further detail of the invention can be appreciated from the following description with reference to the accompanying drawings, in which.

DESCRIPTION OF THE PREFERRED EMBODIMENTS

The investigations leading to the present invention will now be described in more detail.

Figure 1:
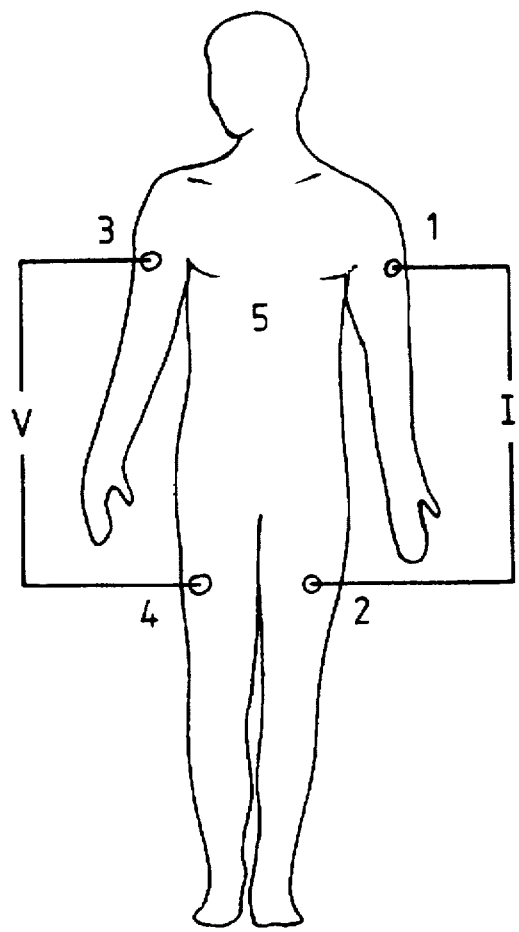
FIG. 1 diagramatically illustrates the tests carried out on a group of human subjects to obtain frequency-based impedance measurements.

Tetrapolar impedance measurements were made as shown in FIG. 1 by applying a sinusoidally varying current of constant 1 mA peak to peak amplitude between the left upper arm 1 and left calf 2 of a human subject and measuring the potential resulting between the right upper arm 3 and right calf 4. The measurements obtained should principally relate to the impedance of the trunk 5. The electrodes used were Ag/AgCl types (Conmed 140–2545 [Trademark]) and the electrode impedances measured were typically <500 ohms at 9.6 kHz.

The current waveform was successively doubled in frequency from 9.6 kHz to 614.4 kHz and each step lasted for 3.33 ms. This allowed a complete set of measurements at 7 frequencies with a 3.33 ms gap between sets to be made in 26.7 ms, thereby giving 37.5 data sets per second. The potentials recorded were first amplified and then de-modulated using a high frequency multiplier to extract the in-phase component of the signal, in other words, the real part of the complex impedance. AC coupling used within the amplifier allowed the signal to settle to better than 0.1% within the 3.3 ms periods. The resulting signal was then low pass filtered (4 pole with 3 dB at 25 Hz) before being digitized at 50 or 200 samples per second to 12 bit resolution and passed to a computer. The A-D interface was a DAS-8PGA8 (Keithley) and the computer a Research Machines 386/20. Data was collected using commercial software (Asyst, EasyestLX, Keithley). The system was calibrated using resistances up to 20 ohms and parallel resistor-capacitor combinations (300 ohms and 10 nF) to represent the electrodes. The measurement accuracy was within 3% over the 7 frequencies.

Twelve normal subjects with no known respiratory or cardiac abnormalities were used for the measurements (Average age 37 years; range 23 years to 51 years; 9 male and 3 females). Although not shown in FIG. 1, the subjects were seated on an insulating surface during the measurements and placed their hands on a wooden bench. Care was taken to see that the knees did not touch during the measurements as this would present an uncontrolled path for current flow.

Two recordings, or measurement sets, were made from each subject, the first recording was 10 seconds duration and the second recording was 40 seconds. During the first recording the subject was asked to inspire total lung capacity and to hold his or her breath for the 10 second recording. During the second recording, each subject again held his or her breath for 10 seconds but was then told to expire and breath normally for an additional 30 seconds. Each recording was collected as 2048 data points.

The first recording was used to measure the real part of the absolute impedance at the seven frequencies and also the amplitude of the cardiac related changes. The second was used to record the amplitude of the impedance change on expiration following the breath hold. Because of the high frame rate of 37.5 s$^{-1}$ the measurements at the 7 frequencies were in effect made simultaneously. The measurements of the amplitudes of the cardiac and respiratory related components were made by printing the waveforms and then manually measuring the peak to peak amplitude of the signals. In every case, the waveforms were digitally low pass filtered at 10 Hz in order to reduce noise. It was found that no attenuation of the cardiac related changes occurred as a result of the filtering.

Figure 2A:
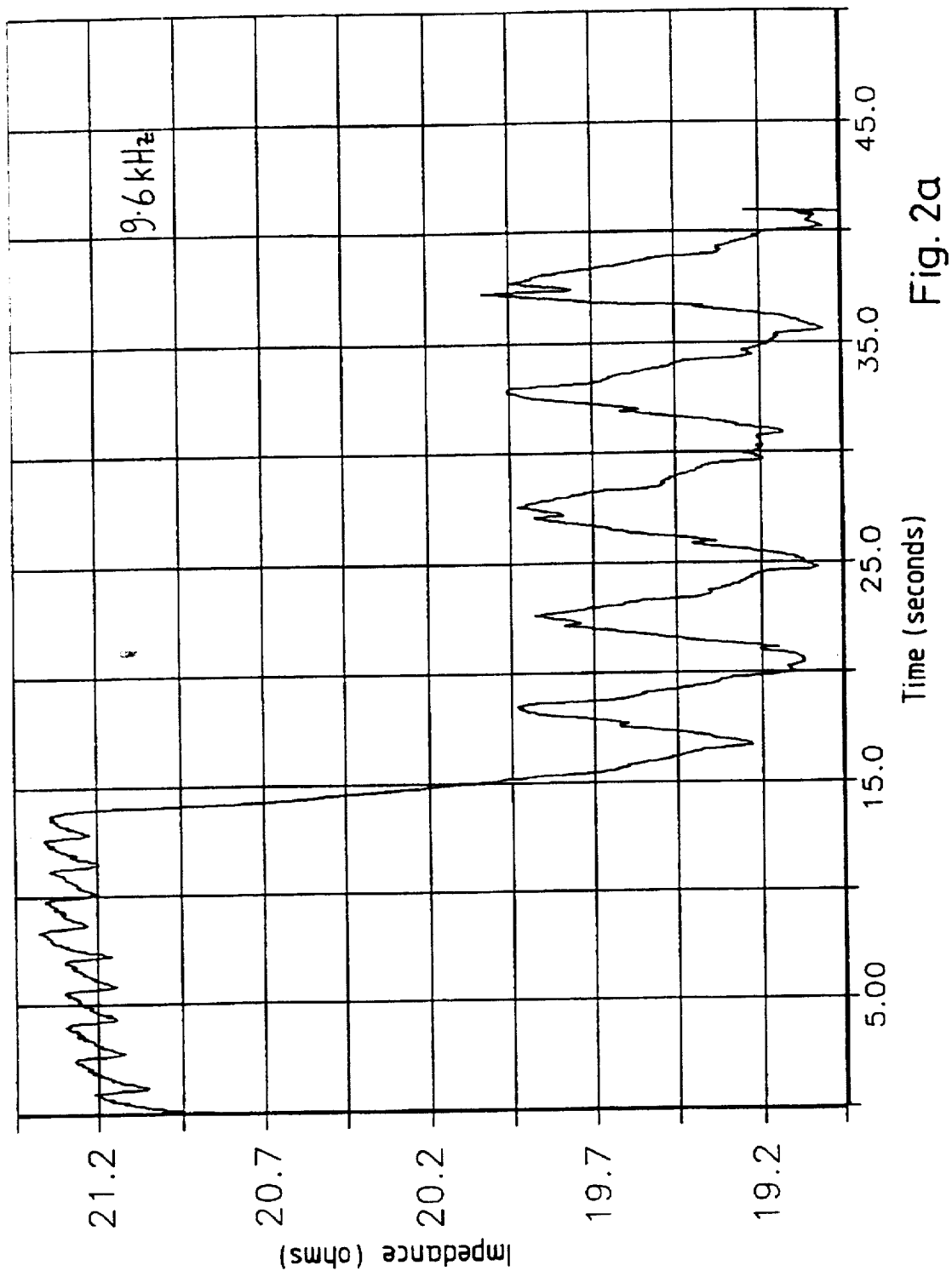
FIGS. 2a and 2b show the results of two of the tests carried out on a subject at two different frequencies.

A trace of the impedance measured at 9.6 kHz from one of the 40 second recordings is shown in FIG. 2a. The cardiac related changes are clearly visible during the first 12 seconds when the breath is held. On expiration the impedance falls and the changes during tidal breathing can be seen. The cardiac changes show a rapid decrease in impedance during systole and then a slower increase during diastole. The ECG was recorded in one subject and confirmed that the rapid decrease in impedance did correspond to the start of cardiac systole.

Figure 2B:
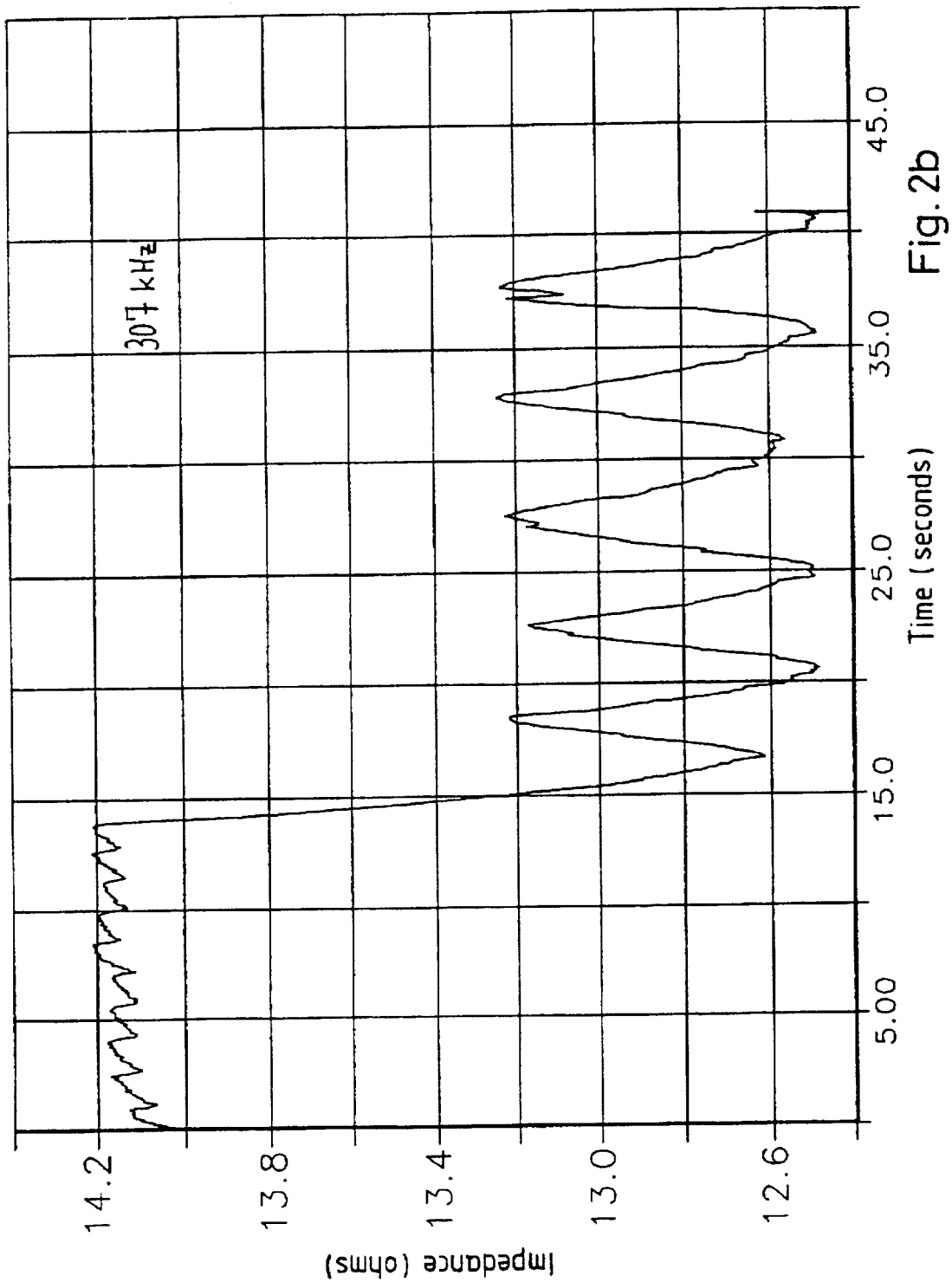

FIG. 2b shows the measurements made at 307 kHz in the same recording as that shown in FIG. 2a. It can be clearly seen that the relative amplitude of the cardiac and respiratory related changes are different at the respective frequencies, the cardiac related changes being smaller in the recording made at 307 kHz.

The group mean values of impedances measured at the 7 frequencies and the amplitudes of the respiratory and cardiac related changes are given in Tables 1 and 2 presented below. The mean impedance and the cardiac related changes were measured during the 10 second breath hold at total lung capacity. The respiratory component was measured from the second recording as the change from total lung capacity to normal tidal breathing. In all cases, it is the real part of the impedance which is shown so that impedances are given as ohms in the case of the respiratory changes and milli-ohms in the case of the cardiac related changes. The recording illustrated in FIGS. 2a and 2b show mean impedances at total lung capacity of about 21.2 ohms at 9.6 kHz and 14.2 ohms at 307 kHz. These figures compare with the group means of 24.56 ohms at 9.6 kHz and 17.81 ohms at 307 kHz. Standard deviations are given for all the measurements.

These standard deviations are quite large because they depend upon the shape and size of the subject as well as on the internal resistivities. In Table 2 normalized results are presented such that 100% represents the measurement at 9.6 kHz. The standard deviations given here are significantly less than in Table 1 because they show only the change in impedance with frequency in each individual.

| Frequency (kHz) | Impedance ($\Omega$) Z | Respiratory component ($\Omega$) $\delta Z_r$ | Cardiac component ($\Omega \times 10^{-3}$) $\delta Z_c$ |
| --- | --- | --- | --- |
| 9.6 | 24.56 ± 4.09 | 1.68 ± 0.43 | 98.4 ± 33.0 |
| 19.2 | 23.93 ± 4.10 | 1.66 ± 0.43 | 89.1 ± 32.5 |
| 38.4 | 22.64 ± 4.08 | 1.62 ± 0.42 | 79.4 ± 32.7 |
| 76.8 | 21.04 ± 3.96 | 1.55 ± 0.41 | 63.5 ± 26.2 |
| 153.6 | 19.35 ± 3.78 | 1.47 ± 0.39 | 54.1 ± 22.5 |
| 307.2 | 17.81 ± 3.50 | 1.37 ± 0.36 | 40.4 ± 17.9 |
| 614.4 | 15.70 ± 2.80 | 1.10 ± 0.30 | 28.2 ± 12.4 |

Table 1, presented immediately above, shows mean data for the 12 subjects. The respiratory component ($\delta Z_r$) is the respiratory related impedance change, i.e. the impedance change between total lung capacity (breath held) and normal tidal breathing. The cardiac component ($\delta Z_c$) is the cardiac related impedance change measured from the peak to peak amplitude of the fluctuating impedance signal at total lung capacity.

| Frequency (kHz) | Impedance (Ω) Z | Respiratory component (Ω) $\delta Z_r$ | Cardiac component (Ω × 10$^{-3}$) $\delta Z_c$ |
|---|---|---|---|
| 9.6 | 100 | 100 | 100 |
| 19.2 | 97.4 ± 1.1 | 98.9 ± 1.2 | 89.9 ± 6.2 |
| 38.4 | 92.0 ± 1.4 | 96.5 ± 2.3 | 78.7 ± 8.9 |
| 76.8 | 85.4 ± 2.0 | 92.1 ± 3.4 | 63.1 ± 9.1 |
| 153.6 | 78.4 ± 2.5 | 87.5 ± 3.8 | 53.7 ± 8.6 |
| 307.2 | 72.2 ± 2.4 | 80.1 ± 5.2 | 40.7 ± 10.5 |
| 614.4 | 64.0 ± 2.1 | 65.4 ± 3.4 | 28.2 ± 6.5 |

Table 2, presented immediately above, shows mean data for the 12 subjects. The values have been normalized to the measurements made at 9.6 kHz before taking the mean for the group.

In all twelve cases, the amplitude of the cardiac related impedance changes ($\delta Z_c$) decreased more rapidly with increasing frequency than did the respiratory related impedance change ($\delta Z_r$). The cardiac change fell from 100% to 28.2% (range 18.6–39.4%). The respiratory change fell from 100% to 65.4% (range 59.8–71.1%). A decrease of impedance with frequency has typically been found in biological tissue, but the difference in the case of the cardiac and respiratory components was unexpected. Subsequent studies by the inventors have confirmed these findings, and tests carried out with the subject following different breathing patterns and using various different configurations of electrodes have also produced results consistent with those described above. Because the relaxation frequency for blood has been quoted as typically 1-3 Mhz it was expected that the cardiac related changes would not fall significantly in amplitude at frequencies up to 600 kHz. Some modelling was carried out in order to investigate this observation of a relatively rapid fall in the amplitude of the cardiac related changes.

Figure 3:
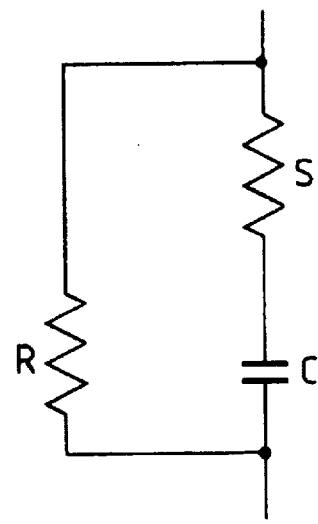
FIG. 3 represents a simple form of electrical equivalent circuit for tissue.

Many studies have used a simple R C combination as shown in FIG. 3 to model tissue impedance. In this case R can be loosely related to extracellular conduction and S to intracellular conduction across the membrane capacitances represented by C. However, a close fit cannot be obtained to in vivo data because there is a dispersion of time constants in tissue; In other words, there is a range of time constants present in tissue.

Some studies have used susceptance vs. conductance plots (H. Kanai, M. Haeno and K. Sakamoto, Electrical measurement of fluid distribution in legs and arms, Medical Progress through Technology, 12,159–170, 1987) based upon the work of Cole and Cole (K. S. Cole and R. H. Cole, Dispersion and Absorption in Dielectrics, Journal of Chemical Physics, 9, 341–351, 1941) to obtain the loci of tissue equivalent circuits. These require measurements to be made over many frequencies and require both real and imaginary components to be available. In the study described above, measurements at only seven frequencies were made and only the real part was recorded. It is possible to record the out-of-phase component, but it is thought that cable capacitances and body capacitance to ground make in vivo recording of the out-of-phase component unreliable. Because of this and the fact that measurements were only made at seven frequencies, the results have been modelled as follows.

A general impedance which establishes a circle in the complex impedance plane can be written:

$$Z = R_\infty + (R_O - R_\infty)/(1+(jf/f_r)^{(1-\alpha)}) \quad (1)$$

where $R_\infty$ is the very high frequency impedance, $R_O$ the low frequency impedance, f the frequency, $f_r$ the relaxation frequency for the tissue and $\alpha$ is the constant which characterizes the Cole-Cole distribution function. Extracting the real part of equation (1) gives:

$$Z(RP) = R_\infty + (R_O - R_\infty) \left[ \frac{1 + (f/f_r)^{(1-\alpha)}\cos(1-\alpha)\pi/2}{[1 + (f/f_r)^{(1-\alpha)}\cos(1-\alpha)\pi/2]^2 + [(f/f_r)^{(1-\alpha)}\sin(1-\alpha)\pi/2]^2} \right] \quad (2)$$

To be consistent with the notation of FIG. 3, $R=R_O$ and $R_\infty=RS/(R=S)$.

Figure 4:
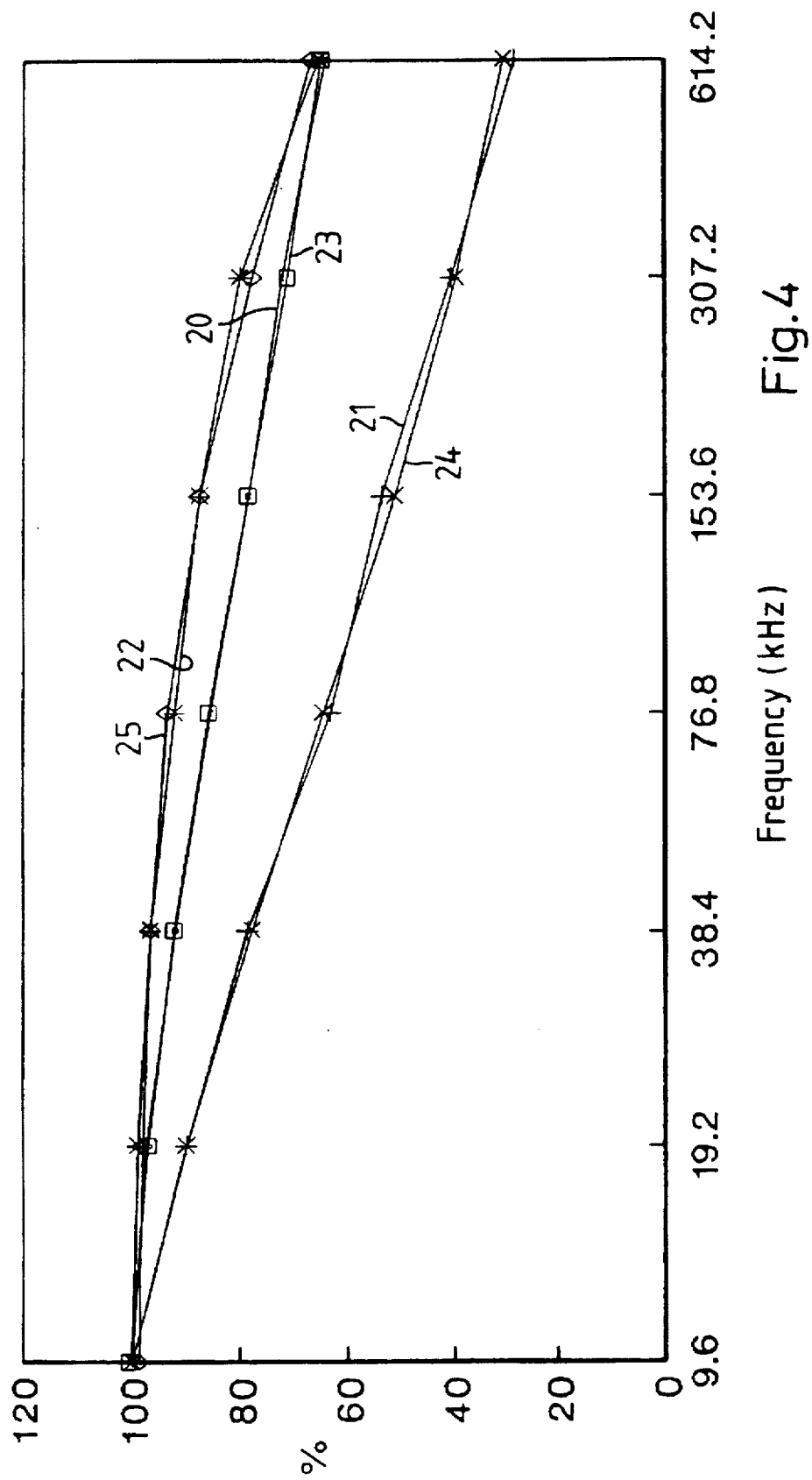
FIG. 4 shows the results of a different way of modelling of tissue impedance characteristics.

This has been used to perform a least square fit to the data of Table 1. Parameters R,S,$f_r$ and $\alpha$ were thus obtained for the total impedance, the respiratory component and the cardiac component. The results of this modelling are illustrated in FIG. 4, which shows both the measured values of the different impedance components and the equivalent values from the model. The curves are measured absolute impedance 20, measured cardiac component 21, measured respiratory component 22, modelled absolute impedance 23, modelled cardiac component 24 and modelled respiratory component 25, all shown as percentages of that measurement at 9.6 kHz.

The modelling shows that the measured data can be modelled very well to equation (2). The following parameters were obtained.

| Total Impedance: | R = 26.13Ω |
| --- | --- |
|  | S = 23.38Ω |
|  | $f_r$ = 158 kHz |
|  | $\alpha$ = 0.39 |
| Respiratory related component: | R = 1.68Ω |
|  | S = 1.44Ω |
|  | $f_r$ = 421.5 kHz |
|  | $\alpha$ = 0.21 |
| Cardiac related component: | R = 118.7Ω |
|  | S = 7.26Ω |
|  | $f_r$ = 86.8 kHz |
|  | $\alpha$ = 0.43 |

It can be argued that it is more logical to see the cardiac and respiratory related components as a perturbation of the base impedance. If the modelling is done in this way, then we can find the equivalent changes in R and S which explain the observations. The results of this are as follows.

| Respiratory related component: | change in R is 1.45Ω |
| --- | --- |
|  | change in S is 3.83Ω |
| Cardiac related component: | change in R is 0.104Ω |
|  | change in S is 0.136Ω |

As can be seen from the results above the measurements of trunk impedance fall with a frequency which can be modelled very well using a Cole-Cole equation. The fall in impedance in an individual is very consistent. However, the differences in absolute impedances between individuals are quite large and probably largely reflect differences in body shape and size. If a simplified model were assumed for the trunk then it would be possible to express the impedance in terms of tissue volume. However, such a simplified model would require so many assumptions that its utility would be questionable.

The results show a significant difference in the way in which the cardiac and respiratory related impedance changes vary with frequency. If a multi-frequency electrical impedance tomographic (EIT) system is used to calculate the impedance spectrum for each pixel, then it is possible to identify cardiac and respiratory signals on the basis of their different frequency behavior. Single frequency EIT imaging has demonstrated images of impedance changes from both the heart and lungs. However, the spatial resolution is poor and in many cases it is not possible to differentiate tissues. The in vivo images published have used a 2-D solution to fit a 3-D problem and the spatial resolution is at best 10% of the imaged diameter. However, based on the present invention, by making multi-frequency measurements, it is possible to identify tissues on the basis of the impedance spectrum and the spectrum of the changes in impedance.

It was expected that the tissue impedance would fall with frequency and that the changes during lung ventilation would fall in a similar manner. However, if the cardiac related changes arise from changes in blood distribution, then perhaps only small changes with frequency would be expected. Blood has no alpha dispersion but a beta dispersion is observed. A relaxation frequency (i.e., the 3 dB frequency corresponding to the mean tissue time constant), for blood of 3 MHz has been suggested (Kanai), and other studies have found values about 1–2 MHz. If these values are correct, then over the frequency range of the measurements of the tests described above (9.6 to 614 kHz), relatively small changes should be seen. The modelling of the cardiac related changes showed a relaxation frequency of 86.8 kHz, which is not consistent with Kanai's figures for blood.

One possible explanation of the observations of the tests described above is that the origin of the cardiac related impedance changes could be the pulsatile blood volume changes in the upper part of the pulmonary tree. These could be shunted by the non-pulsatile lung tissue that has a decreasing impedance at high frequencies, and thus, decreases the relative magnitude of the cardiac related impedance changes. It has been shown that cardiac related impedance changes can be recorded from the area of the lungs, and that these might arise from changes in blood volume in the lungs. Most of these changes are likely to occur in the larger vessels where the pressure waveform is pulsatile, and hence, changes in vessel cross-section occur. Two reasons can be found to identify the lungs as the major possible origin of the cardiac related changes. First, the impedance falls during systole whereas one would expect the impedance of the heart to rise, and second, for a large undispersed volume of blood, such as is found in the heart and major vessels, one might expect to see the high relaxation frequency found from measurements on whole blood. It is, however, not possible to make a straightforward comparison between the frequency dispersion of blood and that of the whole trunk.

Figure 5:
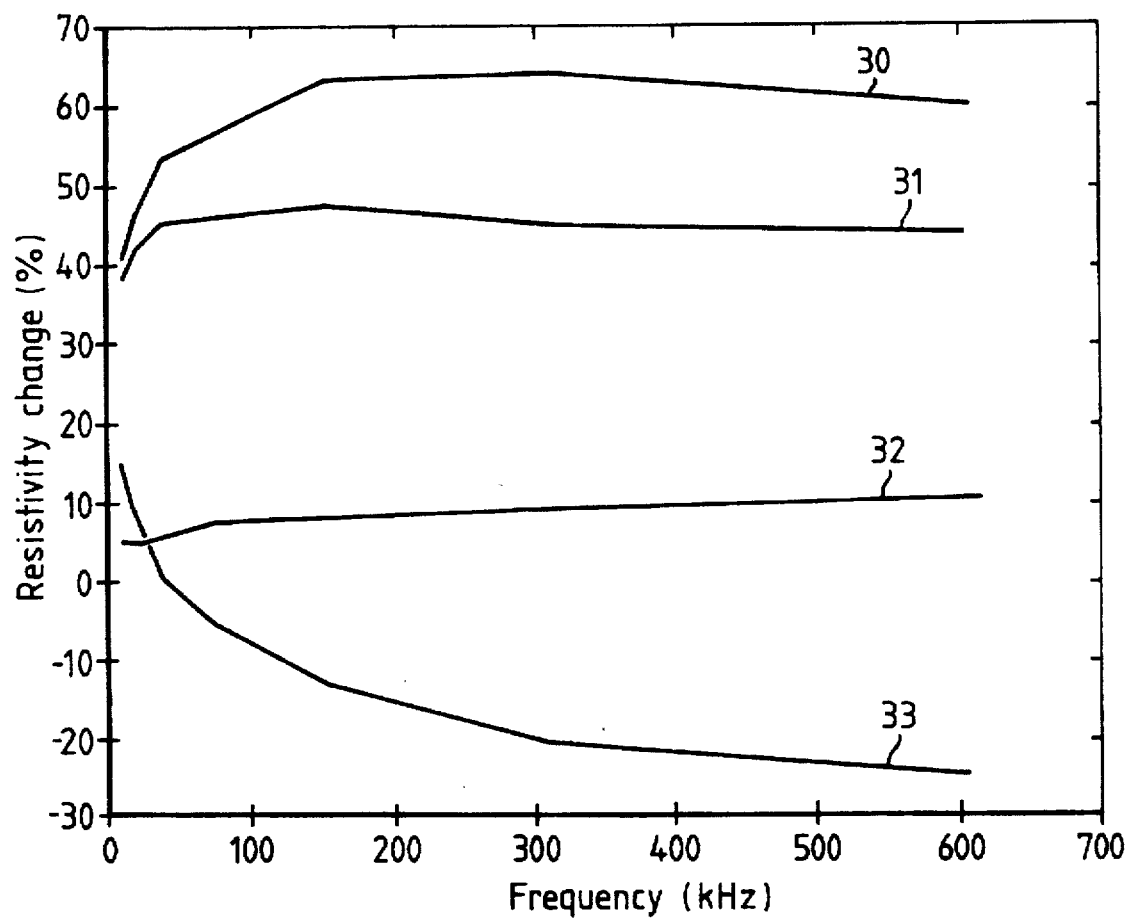
FIG. 5 shows, as a function of frequency, the resistivity change between inspiration and expiration of a human subject associated with different regions of interest within a body.
Figure 6A:
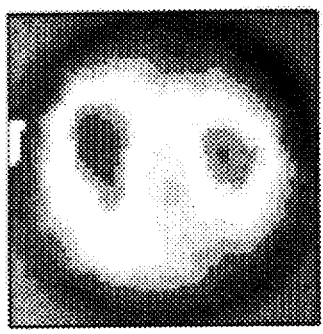
FIG. 6 shows tomographic images of the resistivity change between inspiration and expiration at different frequencies.
Figure 6B:
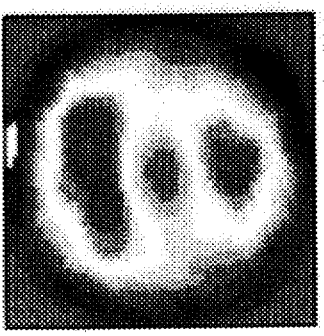
Figure 6C:
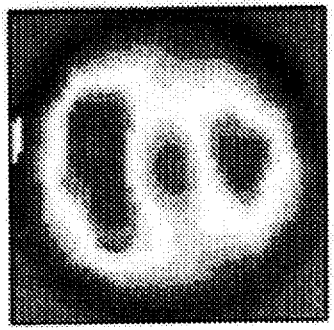
Figure 6D:
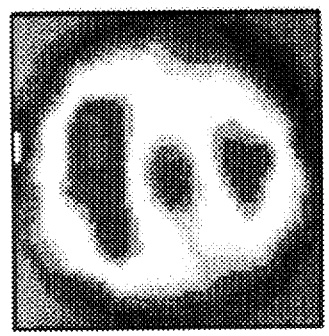
Figure 6E:
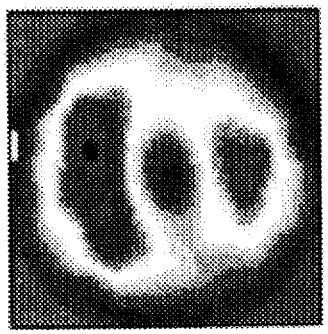
Figure 6F:
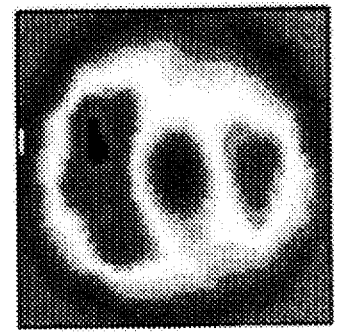
Figure 6G:
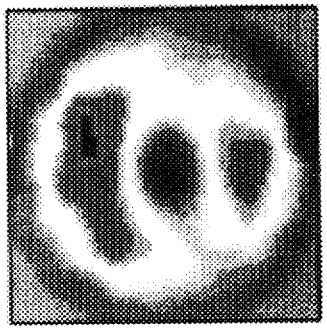
Figure 6H:
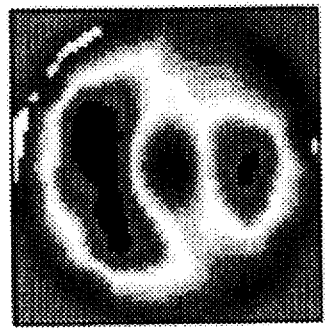

Further investigations have been carried out into the frequency response of the impedance changes associated with different regions of a tomographic image of a cross section of a human trunk. FIG. 5 graphically shows the results of these investigations, the horizontal axis representing frequency and the vertical axis representing the ratio, expressed as a percentage, of the change in resistivity between inspiration and expiration referenced to resistivity on expiration, (Z insp–Z exp)/Z exp.

The subject was told to breath in fully and hold his breath, and then to expire fully and again hold his breath. The four curves 30, 31, 32 and 33 show the frequency response of different areas of clinical interest, and respectively represent the right lung response, the left lung response, the spinal column response, and the response of the central region of the image, which is thought to represent the cardiovascular system.

The curves of FIG. 5 clearly show how, by examining the frequency response of the dynamic impedance changes, selective determination of different parts of the tomographic image is possible. The gradients of the curves, especially in the 0–100 kHz frequency range, show a clear distinction for different anatomical regions of interest. As expected, the response associated with the spinal column is virtually a flat line, as the spinal column exhibits minimal change in state over the respiratory cycle. Any change in this value is probably due to some contamination by lung data in the selected region.

FIG. 6 shows a set of EIT images illustrating the use of the above-mentioned effect. The eight images were produced using a standard EIT technique, the impedance measurements being made effectively simultaneously at eight different electrical signal frequencies, from 9.6 kHz to 1228.8 kHz, successive images representing a doubling of the frequency. The pixel values in the images represent the values of (Z insp–Z exp)/Zexp over the respiratory cycle, i.e., the resistivity change referenced to resistivity at expiration. The images are normalized to the maximum change in the image set. The progressive changes in the images as the frequency is increased illustrate the use of the technique of the invention, such changes being in no way predicted prior to the invention.

The values used to produce the curves at FIG. 5 are taken from these images by selectively localizing regions of interest on an image and determining resistivity values for those regions. More particularly, for each lung region, the image data were examined to find the peak change in resistivity associated with that lung over the respiratory cycle at 9.6 kHz. A region was then determined including pixels displaying a change in resistivity over the cycle of 50% and above of this peak change. This region was assumed to represent the area of that lung. The values used for the curves of FIG. 5 represent mean values over the relevant region. A similar approach was used to fix a central region of the image, and therefore, to produce curve 33 in FIG. 5. For the spinal region, this was fixed by eye from dual frequency static imaging, and again the values used to construct curve 32 in FIG. 5 represent mean values over that region.

The invention has been described and illustrated with reference to a cardiac and respiratory related impedance response. However, it is to be understood that it may also be applied to investigate different parts of the human or animal body where a change in internal state occurs. For example, the technique may find application in investigating the movement of food or fluid through a subject's oesophagus or the movements of a subject's gastric contents. The movement of the contents or peristaltic effects will provide the change in internal state. The technique might also find application outside medical or veterinary areas.

We claim:

1. A method of electrical impedance investigation of a body exhibiting a change in internal state, said method comprising:

applying to the body interrogatory electrical signals at different frequencies;

obtaining first signals representing first electrical impedance measurements at the different frequencies before said change in the internal state of the body;

obtaining second signals representing second electrical impedance measurements at the different frequencies after said change in the internal state of the body, wherein the first and second obtained signals are associated with a variation in two variables, said variables being (i) frequency and (ii) internal state of the body;

determining a change in said impedance measurements over a variation of one of said two variables;

determining a normalized change measurement from said change in said impedance measurements, said change in said impedance measurements being normalized with respect to a chosen reference impedance measurement;

determining a response, over a variation of said other of said variables, to said normalized change measurement; and selectively determining characteristics of a part of said body from said response.

2. A method according to claim 1, wherein the change in the internal state of the body involves a change in geometry of at least part of said body.

3. A method according to claim 1 or claim 2, wherein said first electrical impedance measurements and said second electrical impedance measurements correspond to selected different points in a cyclic change in the internal state of the body.

4. A method according to claim 3, wherein the respective measurements are made at points selected to correspond substantially to peak and trough points in the cyclic change.

5. A method according to claim 1, wherein the obtained signals represent only a real part of the electrical impedance measurements.

6. A method according to claim 1, wherein the electrical impedance measurements are made at frequencies in the kHz range.

7. A method according to claim 6, wherein there is at least one order of numerical difference between the lowest and highest frequency.

8. A method according to any preceding claim 1, wherein the body is a human or animal body of a subject.

9. A method according to claim 8, wherein the body part is an organ or organs of the body.

10. A method according to claim 8 or claim 9, wherein the body has a trunk and the interrogatory electrical signals are applied to said trunk, said part of the body being the heart or at least one lung of the body.

11. A method according to claim 10, wherein said first electrical impedance measurements are made when the subject's breath is held after inspiration and said second electrical impedance measurements are made when the subject's breath is no longer held.

12. A method according to claim 9, wherein the respective signals are obtained by taking measurements in synchronization with a cyclic variation in the state of said part of the body.

13. A method according to claim 1, including using electrical impedance tomography (EIT) techniques to generate images of said part of the body by use of signals representing said characteristics of said part of the body.

14. A method of electrical impedance investigation of a body exhibiting a change in internal state, said method comprising:

applying to the body interrogatory electrical signals at different frequencies;

obtaining first signals representing first electrical impedance measurements at the different frequencies before said change in the internal state of the body;

obtaining second signals representing second electrical impedance measurements at the different frequencies after said change in the internal state of the body;

selectively determining characteristics of a part of said body from a response to a change in frequency of a differential variation between the first and second signals;

wherein the body is a human or animal body of a subject;

wherein said electrical signals are applied to the trunk of the body and the part of said body is the heart or at least one lung of the body; and wherein said first electrical impedance measurements are made when the subject's breath is held after inspiration and said second electrical impedance measurements are made when the subject's breath is no longer held.

15. A method of electrical impedance investigation of a body exhibiting a change in internal state, said method comprising:

applying to the body interrogatory electrical signals at different frequencies;

obtaining first signals representing first electrical impedance measurements at the different frequencies before said change in the internal state of the body;

obtaining second signals representing second electrical impedance measurements at the different frequencies after said change in the internal state of the body;

selectively determining characteristics of a part of said body from a response to a change in frequency of a differential variation between the first and second signals; and wherein electrical impedance techniques are used to generate images of said part of said body by use of signals representing said characteristics of said part of said body.

* * * * *